(12) United States Patent
Backer et al.

(10) Patent No.: US 7,211,662 B2
(45) Date of Patent: *May 1, 2007

(54) SOLUBLE HIGHLY BRANCHED GLUCOSE POLYMERS AND THEIR METHOD OF PRODUCTION

(75) Inventors: Daniel Backer, Saint-Venant (FR); Marie-Helene Saniez, Saint Andre (FR)

(73) Assignee: Roquette Freres, Lestrem (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/066,423

(22) Filed: Feb. 28, 2005

(65) Prior Publication Data

US 2005/0142167 A1 Jun. 30, 2005

Related U.S. Application Data

(62) Division of application No. 10/454,225, filed on Jun. 4, 2003, now Pat. No. 6,861,519.

(30) Foreign Application Priority Data

Jun. 6, 2002 (FR) .................................. 02 06952

(51) Int. Cl.
- C08B 30/00 (2006.01)
- C08B 30/18 (2006.01)
- C08B 30/20 (2006.01)

(52) U.S. Cl. .................. 536/102; 536/103; 536/123.1; 536/55.1; 536/124; 426/656

(58) Field of Classification Search ................ 536/102, 536/103, 123.1, 55.1, 124; 426/658

See application file for complete search history.

(56) References Cited

U.S. PATENT DOCUMENTS 4,454,161 A * 6/1984 Okada et al.
4,840,807 A * 6/1989 Yoshida et al. ............... 426/48
5,612,202 A * 3/1997 Brumm
5,886,168 A * 3/1999 Brumm

FOREIGN PATENT DOCUMENTS

| EP | 0 207 676 B1 | * | 6/1986 |
| JP | 51101141 | * | 9/1976 |
| WO | 82/03329 | * | 10/1982 |
| WO | 95/22562 | * | 8/1995 |

OTHER PUBLICATIONS

Yabuki et al. ; JP 51101141 (Sep. 7, 1976) (Abstract Sent).*
A Derwent abstract of FR 2 792 941 A.*
A Derwent abstract of EP 1 006 128.*
A Derwent abstract of JP 2001011101.*
An English abstract of WO 00/18893.*
An abstract from Food Science & Technology—10 (1999) 345-355—L.M. Marchal et al—entitled *Toward a rational design of commercial maltodextrins*—2000 Elsevier Science Ltd.*
Patent abstract of Japan vol. 2002, No. 2, Apr. 2, 2002 & JP 2001 294601 A (Akita Prefecture), Oct. 23, 2001 (abstract) and database WPI Week 200218 Derwent Publication Ltd., London, GB; AN2002-14411 (abstract).*

* cited by examiner

*Primary Examiner*—Shaojia Anna Jiang
*Assistant Examiner*—Michael C. Henry
(74) *Attorney, Agent, or Firm*—Young & Thompson

(57) ABSTRACT

The invention relates to soluble highly branched glucose polymers having a reducing sugar content of less than 1%, characterized in that they have a level of α-1,6 glucoside bonds greater than 10%, preferably of between 12 and 30%, a Mw value of between $0.35 \times 10^5$ and $2 \times 10^5$ daltons, and an osmolality having a value of between 1 and 15 mOsm/kg. The invention also relates to their method of production and their applications in the Paper-Carton, Textiles, Cosmetics, and particularly Pharmaceutical and Food industries, and still more particularly in the fields of enteral and parenteral nutrition, peritoneal dialysis as a glycemia inhibiting and/or regulating agent, as an energy source during physical activities and as a digestion regulating agent.

19 Claims, No Drawings

SOLUBLE HIGHLY BRANCHED GLUCOSE POLYMERS AND THEIR METHOD OF PRODUCTION

This application is a division of application Ser. No. 10/454,225, filed on Jun. 4, 2003 now U.S. Pat. No. 6,861,519, the entire contents of which are hereby incorporated by reference.

The invention relates to soluble highly branched glucose polymers having a reducing sugar content of less than 1% and having a remarkably high content of α-1,6 glucoside bonds, which is greater than 10%, for a very narrow molecular weight distribution, which is between $0.3 \times 10^5$ and $2 \times 10^5$ daltons, and a very low osmolality, which is between 1 and 15 mOsm/kg.

These soluble branched glucose polymers moreover have a low viscosity and an absence of retrogradation, even after cold storage after long periods of time.

The invention also relates to a method for manufacturing said soluble highly branched glucose polymers.

It also relates to compositions comprising such soluble branched glucose polymers which it is possible to use in numerous industrial applications, and in particular in the food and especially pharmaceutical industries.

The glucose polymers which are industrially accessible are in particular prepared by hydrolysis of natural or hybrid starches and of their derivatives.

Standard starch hydrolyzates are thus produced by acid or enzymatic hydrolysis of starch from cereals or tubers. They are in fact a mixture of glucose and glucose polymers of extremely varied molecular weights.

These starch hydrolyzates (dextrins, maltodextrins, and the like) which are produced in industry (with a certain Degree of Polymerization or mean DP) consist of a wide distribution of saccharides containing both linear structures (α-1,4 glucoside bonds) and branched structures (α-1,6 glucoside bonds).

These starch hydrolyzates, and in particular the maltodextrins, are used as a transporter or a filler, as a texturing agent, as a spray-drying support, as a fat replacer, as a film-forming agent, as a freezing regulator, as an anticrystallizing agent, or for their nutritional value.

It is moreover known to persons skilled in the art that the saccharide composition of maltodextrins determines both their physical and biological properties.

Accordingly, their hygroscopicity, their fermentability in food products, their viscosity, their sweetening character, their stability, their gelling character and their osmolality are criteria which are conventionally determined for their various fields of application.

Basic knowledge of the physicochemical behavior of these saccharides thus leads to their being incorporated, for example, into drinks for athletes, liquid drinks with limited solubility, parenteral and enteral fluids or in foods for diabetics.

As a result, for these different applications, various physical and biological properties are required.

It is for example known that the rate of absorption of these saccharides is determined by the rate of gastric emptying and the rate of intestine adsorption, the regulation of which is provided by the osmolality of said saccharides.

At the intestinal level, the maltodextrins are hydrolyzed by pancreatic α-amylase, which leads to their size being reduced to limit dextrins, and a number of enzymes linked to the intestinal mucous membrane (maltase, sucrase and α-dextrinase) continue to hydrolyze the linear and branched saccharides to glucose.

While glucose easily crosses the intestinal barrier (passive diffusion), the same is not true of saccharides with a low DP. Accordingly, linear oligosaccharides will be absorbed more quickly than branched oligosaccharides, although maltose and maltotriose are absorbed more quickly than glucose.

The colon bacteria will ferment all the carbohydrates which are not adsorbed by the small intestine. Excessive fermentation by these bacteria will result in intestinal disorders such as cramps and flatulence.

It is also known that the osmolality influences the rate of absorption/secretion of water in the small intestine. The higher the osmolality of a compound, the more it induces entry of fluid into the intestine and leads to serious stomach upsets (osmotic diarrhea), with concomitant loss of fluid and of electrolytes.

The osmolality of a solution is equal to the quantity of moles dissolved per kg of water, which implies that at the same concentration by dry weight, the osmolality of a conventional maltodextrin increases with a decrease in its DP.

In general, maltodextrins are well absorbed by the human body, but under more extreme physical conditions, such as sports exercise or disease, a better supply of carbohydrates should be provided.

For example, in athletes, a drink consumed during physical activity which requires a lot of effort should instantly provide the energy and the water necessary to compensate for the loss of fluid through perspiration.

It results from what has been stated above that a composition which is balanced in relation to carbohydrates is essential in order to obtain such a result.

One solution which is conventionally proposed for the optimum drink is to choose short linear oligosaccharides with a DP of 3 to 6, since they are absorbed at the highest rate, while retaining the osmolality at a moderate level, thus preventing the loss of fluids and side effects such as diarrhea and cramps.

However, these compositions have the disadvantage of constituting energy sources which are too instantly assimilated by the body, which results in difficulties in maintaining a constant energy supply over long periods of time.

Patent application WO 95/22,562 thus proposes novel starch derivatives intended to supply energy for preparation of or after physical effort.

They are dextrins, characterized by their molecular weights of between $15 \times 10^3$ and $10^7$ daltons, and a degree of 1,6 glucoside branching of between 2 and 8%, preferably between 3 and 7%, which ensures renewal of the energy reserves in the form of glycogen.

In their liquid form, these particular dextrins cross into the small intestine after rapid gastric emptying. This route is moreover regulated by the osmolality of said dextrins.

A high osmolality means here that the substances of low molecular weight bind to water, which make the transport of water and of nutrients into the cell difficult. The osmolality of blood is about 300 mOsm/l, and, with the aim of facilitating the transport of nutrients, it is desirable for the osmolality of the substance to be considerably below this value.

A dextrin according to WO 95/22,562, having an average molecular weight of about 720 000 and a degree of branching of about 4%, is described as having an osmolality of 20 mOsm/kg sol.

However, these dextrins are prepared by acid treatment of native starch, more particularly of potato starch, under high temperature conditions, i.e. 110 to 140° C., and in a reaction time of 1 to 15 hours, which leads to a 1,6 degree of branching, which corresponds both to α-1,6 and β-1,6 glucoside bonds.

These atypical glucoside bonds are not digested by the enzymatic systems of the intestine, and can lead to the accumulation of indigestible residues which certain undesirable bacteria will assimilate.

In another field of application, maltodextrins are often added to drinks in order to increase their viscosity. However, in those containing alcohol, the supply of MD with a high DP can cause problems of stability of the mixture.

Another solution which consists in adding maltose or glucose leads nevertheless to an additional sweet taste being given to the mixture, which is not always desirable. Furthermore, these small oligosaccharides can serve as fermentation substrates for undesirable microorganisms.

The maltodextrins most suitable for this field of application must therefore combine and balance the parameters of "nonsweetness", viscosity and stability.

In the field of parenteral solutions, nutritive solutions are designed in order to maintain a patient in good health and provide them with nutrients when they cannot be fed via their normal digestive system.

Since the solutions are directly supplied by the venous route, they must be isotonic and the glucose supply is limited.

To provide a daily energy of 10 000 kJ, it is described in an article from FOOD Science Technology of 1999, pp. 345–355 by MARCHAL et al., that it would be necessary to infuse 14 liters of isotonic glucose solution (5% weight/volume of glucose), which widely exceeds human capacities.

The intake of more concentrated glucose or fructose solutions (10 to 20% weight/volume) is possible, but not for long periods.

It is possible to administer linear saccharides with a DP of between 2 and 5, since these saccharides are hydrolyzed by maltases in the kidney, and the glucose released is then reabsorbed. Accordingly, the use of short linear oligosaccharides makes it possible to supply sufficient energy in an isotonic solution, without overhydrating the patient.

Moreover, since linear oligosaccharides with a DP of less than 7 are stable in solution over long periods of time, it is conventionally chosen to vary the DP between 2 and 7 in order to make it possible to constantly supply the patients, over these long periods, with all necessary energy.

However, this solution is not completely satisfactory, and it only envisages the exploitation of linear glucoside structures.

As for enteral nutrition, it involves drinks which may either be injected orally, or administered via a tube into the stomach or the small intestine.

For these enteral fluids, the major problem is diarrhea, due to an excessively high osmolality. In principle, the same solution as that found for athletes may also apply here.

Conventionally, maltodextrins containing a complex mixture of linear and branched saccharides, with a DE of 10 to 20, are therefore used, but without however giving complete satisfaction.

Specialists in these fields of application seek the solution to these technical problems in the production of branched structures derived from starch.

Amylopectin, the main constituent of starch, becomes organized around linear α-1,4 bonds and α-1,6 bonds which become crosslinked therewith. Knowledge of the microstructures has demonstrated that these two types of bond are not uniformly distributed, but that regions with very dense α-1,6 bonds coexist with regions consisting solely of α-1,4 bonds.

It has been proposed, in U.S. Pat. No. 4,840,807, or JP patent application 11/187,708, to extract only the regions with dense α-1,6 bonds as source of slowly absorbed carbohydrates, since the α-1,6 bonds are more difficult to degrade than the α-1,4 bonds.

Two families of products have thus been developed. The first involves limit dextrins prepared by degradation of the regions with α-1,4 bonds with an α-amylase alone, and dextrins prepared by degradation of the regions with α-1,4 bonds by the simultaneous action of an α-amylase and a β-amylase.

The resistance of these limit dextrins to human digestive enzymes makes it possible to use them to regulate digestion, but also to control glycemia (application for diabetic diets). This effect is attributed to slowing of the rate of digestive adsorption.

However, these compounds have the disadvantage of having a very low molecular weight (between 10 000 and 55 000 daltons), which limits their exploitation in other fields of application.

EP patent 207,676 teaches that, for use in continuous and ambulatory peritoneal dialysis, starch hydrolyzates are preferred which form clear and colorless solutions at 10% in water, having Mw of $5 \times 10^3$ to $10^6$ daltons and a low polydispersity index or Ip.

This results in compositions which predominantly contain glucose polymers of high molecular weight between $5 \times 10^3$ and $5 \times 10^5$ daltons), which do not contain or which contain very little glucose or oligosaccharides with a DP of less than or equal to 3, and no or very little glucose polymers with a Mw greater than $10^6$ daltons.

It can easily be understood for this application that monomers or polymers of low molecular weight rapidly cross the peritoneal wall and are thus of no lasting benefit for the creation of an osmotic pressure gradient, and that polymers of very high molecular weight, which have no osmotic power, should be avoided and should even be prohibited since they are potentially dangerous if they happen to precipitate following their retrogradation.

Peritoneal dialysis consists in introducing a dialysis solution into the peritoneal cavity by means of a catheter. After a certain period, an exchange of solutes occurs between the dialyzate and the blood. The use of a suitable osmotic agent allows drainage of excess water from the blood to the dialyzate.

The standard method in peritoneal dialysis for removing excess water (ultrafiltration) and of solutes from the body in case of renal deficiency consisted in using a dialysis solution which has been made hypertonic in relation to the plasma by adding glucose as osmotic agent. The flow across an ideal semipermeable membrane is mainly determined by the total number of particles of solute (osmolality) which are present in the solution, independently of their size. By contrast, in the case of a biological membrane such as the peritoneal membrane, the flow depends solely on the solutes not crossing or only rarely crossing the membrane and is not therefore necessarily linked to the total osmolality of the solution. Additionally, the capacity of the solutes to cross the membrane is characterized by the shape of the molecules and their ionic charge, and by their size.

The choice of an ideal osmotic agent is delicate: the latter should allow an osmotic gradient so as to displace the water, and the toxic substances from the blood to the dialysis solution through the peritoneum. It should also be nontoxic and biologically inert, while being metabolizable by the body, a portion thereof being assimilated in the blood. It should not cross the peritoneal membrane too rapidly, so as to durably maintain an ultrafiltration gradient without accumulating undesirable substances in the blood.

In its EP patent 667,356, the Applicant Company proposed a method for manufacturing, from waxy starch, a starch hydrolyzate which is completely soluble in water and which has a low polydispersity value of less than 2.8, and a Mw of between $5 \times 10^3$ and $1 \times 10^6$ daltons.

This method consists in hydrolyzing, by an acid route, a starch milk consisting exclusively of amylopectin, and then in supplementing this acid hydrolysis with an enzymatic hydrolysis using a bacterial α-amylase, and chromatographing on macroporous strong cationic resins in alkali or alkaline-earth metal form.

It should be noted that at the time, the Applicant Company recommended using only starches almost exclusively composed of amylopectin and commonly called waxy starches as raw material in said method, the starches containing a non-negligible proportion of amylose not being suitable.

This starch hydrolyzate, also called icodextrin, allowed a significant reduction in the daily absorption of glucose previously used as osmotic agent in dialysis solutions, thus constituting a potential advantage for the treatment of diabetic and obese patients for whom the calorie supply is a critical factor. This could however be further improved by using an osmotic agent which is less glycemic, and whose osmotic power would last longer, which would make it possible to significantly lighten the dialysis treatment procedure. Indeed, having improved the yield of dialyzates, the rate at which the dialysis bags are changed would be reduced, which constitutes a definite improvement in the patient's quality of life.

Thus, the ideal carbohydrate in peritoneal dialysis should:
- be soluble in water
- exert osmotic pressure
- have a low viscosity
- not undergo retrogradation
- induce low kinetics of appearance of glucose in the system circulation
- be slowly hydrolyzed by amylase so as to exert a lasting osmotic pressure.

Indeed, in relation to the latter point, the fate of the osmotic agents administered in solution into the peritoneal cavity in renal insufficiency sufferers is determined by its stability in the peritoneal fluid, the degree of absorption in the system circulation and the rate of hydrolysis by amylase. However, the prior art osmotic agents have the disadvantage of being rapidly hydrolyzed.

Likewise, so-called resistant starches have been proposed as glycemia regulating agents. However, these are generally not stable in the compositions, cannot be sterilized, which ultimately causes a loss of product, and they can be fermented and do not therefore supply the expected amount of calorie.

From the preceding text, it is evident that an unsatisfied need therefore exists to have glucose polymers which exhibit remarkable properties, in particular in terms of stability, solubility and possibly viscosity, and which thereby confer on the products containing them higher capacities of shelf life, controlled digestibility, which allows the use thereof in fields as varied as peritoneal dialysis, enteral or parenteral nutrition, as glycemia inhibitor and/or regulator, as energy supply during physical activities and as digestion regulator.

The Applicant Company has had the merit of reconciling all these objectives which were up until now reputed difficult to reconcile, by devising and producing, at the cost of numerous research studies, novel soluble highly branched glucose polymers.

The soluble highly branched glucose polymers in accordance with the invention, which have a reducing sugar content of less than 1%, are thus characterized in that they possess a level of α-1,6 glucoside bonds greater than 10%, preferably of between 12 and 30%, a Mw, determined by light scattering, having a value of between $0.3 \times 10^5$ and $2 \times 10^5$ daltons, and an osmolality, determined according to a test A, having a value of between 1 and 15 mOsm/kg.

The soluble branched glucose polymers in accordance with the invention have a low reducing sugar content.

The determination of the reducing power of the branched glucose polymers in accordance with the invention, by any method moreover known to a person skilled in the art, leads to values below 1%.

The level of α-1,6 glucoside bonds in the soluble branched glucose polymers in accordance with the invention is determined by proton NMR analysis. The level of branching is then expressed in percent, corresponding to the quantity of proton signal carried by the C1 of an anhydroglucose unit which binds another anhydroglucose unit by an α-1,6 bond, when a value of 100 has been given to all the signals of the protons carried by all the C1 atoms of the glucose residues of said soluble glucose polymers.

Under these conditions, it is determined that the soluble highly branched glucose polymers in accordance with the invention have a content of α-1,6 bonds which is greater than 10%, preferably of between 12% and 30%.

This content of α-1,6 bonds confers on any highly branched glucose polymer in accordance with the invention a particular structure, in terms of branching and/or length of branched chains in relation to the starch or to the starch derivative from which it is derived.

This particularly high content of α-1,6 glucoside bonds makes the highly branched glucose polymers according to the invention difficult to digest, which contributes to their being able to be used as digestion regulating agent and as glycemia inhibiting agent, as stated above.

They can therefore be usefully offered to diabetics or to predisposed subjects as foods, drinks or nutritional aids which have the role of inhibiting the increase in glycemia.

The soluble highly branched glucose polymers in accordance with the invention also exhibit the absence of retrogradation in aqueous solution and a remarkable stability.

This property makes the branched glucose polymers in accordance with the invention most naturally destined for compositions which can be used in the food industry, which thereby exhibit high stabilities during storage.

Another advantage of the invention is to allow the production of a finished product which can be used for example as an instant binder in refrigerated or deep-frozen products.

The determination of the molecular masses of the soluble branched glucose polymers in accordance with the invention is carried out by measuring the weight-average molecular masses (Mw).

This value is obtained by steric exclusion chromatography on PSS SUPREMA 100 and PSS SUPREMA 1000 columns mounted in series and coupled to a light scattering detector.

The branched glucose polymers in accordance with the invention thereby have a Mw value of between $0.3 \times 10^5$ and $2 \times 10^5$ daltons.

The soluble glucose polymers in accordance with the invention also have a remarkably low osmolality.

The test A consists in determining the osmolality of a solution containing 100 g on a dry basis of highly branched glucose polymers in accordance with the invention placed in 1 kg of water.

The measurement of the osmolality of this solution is then carried out on a FISKE® ASSOCIATES MARK 3 osmometer, following the manufacturer's specifications.

The branched glucose polymers in accordance with the invention thereby have a remarkably low osmolality value of between 1 and 15 mOsm/kg.

No glucose polymer exists, to the knowledge of the Applicant Company, which possesses such an osmolality value, for products which moreover have a level of branching and molecular weight as defined.

Indeed, comparative measurements carried out on conventional maltodextrins having a dextrose equivalent (DE) of between 5 and 20 show osmolality values of between 25 and 85 mOsm/kg.

Other measurements, performed on limit dextrins as defined above by treating starch liquefied with α-amylase, which are marketed under the name BLD 8 by SANMATSU, give for a molecular weight of between 0.4 and $0.5 \times 10^5$ daltons and an α-1,6 branching content of between 8 and 9%, an osmolality value of more than 35 mOsm/kg.

This very low osmolality value thus confers on the highly branched soluble polymers in accordance with the invention properties which allow them to be used in preparations intended for athletes, to replace the energy sources which they need for physical efforts over long periods.

However, these compositions can also and in particular be advantageously used for patients who can no longer take in food normally, in the context of enteral and parenteral nutrition.

Moreover, combined with this property of low osmolality, their lack of retrogradation, their molecular weight profile and their low polydispersity value makes these highly branched glucose polymers in accordance with the invention perfect candidates as osmotic agents for applications in peritoneal dialysis, as will be exemplified below. The Applicant has moreover demonstrated that these polymers in accordance with the invention have a resistance to alpha-amylase which provides significant advantages compared with the prior art polymers, for a similar molecular weight, since they are less glycemic and have an osmotic power which lasts longer, thus allowing their use in long dialysis treatments.

Advantageously, the highly branched glucose polymers in accordance with the invention may be classified into three subfamilies according to their osmolality.

The first subfamily covers the highly branched polymers which have, for a Mw determined by light scattering having a value of between $0.5 \times 10^5$ and $1.5 \times 10^5$ daltons, an osmolality, determined according to the test A, at least equal to 1 and less than 2 mOsm/kg.

The second subfamily covers highly branched polymers which have, for a Mw determined by light scattering having a value of between $0.5 \times 10^5$ and $0.8 \times 10^5$ daltons, an osmolality, determined according to the test A, at least equal to 2 and less than 5 mOsm/kg.

The Applicant Company has additionally found branched glucose polymers belonging to the two subfamilies which further have a remarkably high α-1,6 branching level, i.e. of between 15 and 30%.

The third subfamily covers highly branched polymers which have a Mw determined by light scattering of between $0.3 \times 10^5$ and $0.7 \times 10^5$ daltons and an osmolality, determined according to the test A, at least equal to 5 and less than 15 mOsm/kg.

To prepare the soluble branched glucose polymers in accordance with the invention, the following succession of steps are carried out which consist in:

a. preparing an aqueous starch suspension or a solution of starch derivative having a dry matter content at least equal to 1% by weight, preferably from 10 to 50% by weight,
b. treating said suspension or said solution with at least one branching enzyme at a temperature between 25 and 80° C. for a period of 1 to 24 hours,
c. causing at least one enzyme chosen from the group consisting of α-amylase, β-amylase, amyloglucosidase and α-transglucosidase to act on the suspension or on the solution thus obtained,
d. carrying out a fractionation using at least one technique chosen from the group comprising membrane separations or chromatographies, so as to recover the high molecular weight fractions,
e. collecting the branched glucose polymers thus obtained.

The starch is introduced in suspension, or the starch derivatives in aqueous solution, at a dry matter content at least equal to 1% by weight, preferably from 10 to 50% by weight.

The choice of a source, or of a quality of starch or of its particular derivatives, is only of a relative importance.

In fact, the Applicant Company has developed a novel method, which makes it possible to obtain the highly branched glucose polymers in accordance with the invention, for example which are applicable in peritoneal dialysis, which does not require being limited to a particular type of starch, in this case a starch rich in amylopectin.

It is therefore possible to choose the natural or hybrid starch obtained from potato, potato with a high content of amylopectin (waxy starch), pea, rice, cassava, wheat, corn, corn or wheat rich in amylopectin (waxy corn or wheat), corn with a high content of amylose, cuts or fractions which can be made or obtained from starches, such as amylose, amylopectin, particle size fractions known to persons skilled in the art by the terms wheat starch "A" and wheat starch "B", and mixtures of at least any two of the abovementioned products.

The starch derivatives may be understood to mean modified starches obtained from enzymatic, chemical and/or physical modification, in one or more steps, of this starch.

The starch derivatives may be in particular starches modified by at least one of the known techniques of esterification, etherification, crosslinking, oxidation, alkaline treatment, acid and/or enzymatic hydrolysis (responsible for the maltodextrins and dextrins).

The Applicant Company has found that the highly, branched glucose polymers in accordance with the invention can be easily synthesized from starches, or from their derivatives, which already have a branching level at least equal to 1%.

This starch suspension, or this solution of starch derivatives, may then be optionally subjected to a particular cooking treatment, which consists in treating it at a temperature of greater than 130° C., preferably of between 140 and 150° C., at a pressure of more than 3.5 bar, preferably of between 4 and 5 bar, for 30 seconds to 15 minutes, preferably for 1 to 5 minutes.

This treatment is advantageously carried out in a jacketed tubular cooker heated by a thermal fluid, which equipment can be easily obtained by persons skilled in the art.

The second step of the method in accordance with the invention consists in treating said starch suspension or said solution of starch derivative with a branching enzyme.

Advantageously, 50 000 to 500 000 U of purified branching enzyme are used per 100 g on a dry basis of starch or of starch derivative, at a temperature of between 25 and 95° C., preferably at a temperature of between 70 and 95° C., for a period of 1 to 24 hours.

The expression branching enzymes is understood to mean, for the purposes of the invention, the branching enzymes chosen from the group consisting of glycogen branching enzymes, starch branching enzymes and any mixtures of these enzymes.

More particularly, these branching enzymes are extracted from organisms and/or microorganisms chosen from the group consisting of glycogen branching enzymes, starch branching enzymes and any mixtures of these enzymes.

The Applicant Company prefers, in order to carry out this treatment with a branching enzyme, to follow the teaching of its patent application WO 00/18,893.

This step leads to the production of soluble branched glucose polymers, but with a content of α-1,6 glucoside bonds at best equal to 10%.

To increase this value and to reach levels of α-1,6 bonds of up to 30%, the Applicant Company found that it is necessary to carry out an additional enzymatic treatment, and that is what constitutes the third step of the method for producing the soluble highly branched glucose polymers in accordance with the invention.

This third step consists in causing at least one enzyme chosen from the group consisting of α-amylase, β-amylase, amyloglucosidase and α-transglucosidase to act on the suspension or the solution treated with a branching enzyme thus obtained.

The conditions for action (temperature and pH) of the different enzymes used in the method in accordance with the invention are chosen from the following (the quantities are determined in relation to the substrate considered, as will be exemplified below):

α-amylase: of the LYSASE 2000 type from GENENCOR, at a temperature of 55 to 65° C., pH of 6.5 to 6.7, for 30 minutes to 1 hour;

β-amylase: of the SPEZYME BBA type from GENENCOR, at a temperature of 40° C., pH of 4.9 to 5, for 1 h 30 min to 2 hours;

amyloglucosidase: either of the OPTIDEX L300 A type from GENENCOR at a temperature of 55° C., pH of 4.7, or of the A-7420 type from SIGMA at a temperature of 50° C. to 60° C., pH from 4.7 to 4.9; for 1 h 30 min to 2 hours;

α-transglucosidase: of the α-TGase type from L-AMANO at a temperature of 55° C., pH from 5 to 5.2, for 1 hour.

The enzymes used may be of bacterial or fungal origin.

At the end of this additional treatment, the soluble highly branched glucose polymers are obtained in the form of a mixture with their products of enzymatic degradation, predominantly consisting of glucose, maltose and/or isomaltose, as will be exemplified below.

The fourth step of the method consists in carrying out a fractionation using a technique chosen from the group comprising membrane separations and chromatographies, so as to recover the high molecular weight fractions and the low molecular weight fractions.

The high molecular weight fractions correspond to the highly branched glucose polymers in accordance with the invention, while the low molecular weight fractions make it possible to obtain, with an excellent yield, compositions rich in maltose and/or isomaltose.

Advantageously, a fractionation technique is chosen from the group consisting of the ultrafiltration membrane separation technique and by the chromatographic separation technique on a gel type support.

In a first embodiment of this fourth step of the method, the fractionation is performed using an ultrafiltration membrane separation technique, using a membrane having a cut-off at least equal to 3000 daltons, preferably at least equal to 5000 daltons.

The high molecular weight fractions corresponding to the highly branched glucose polymers, equal to the ultrafiltration retentate, then represent about 60% of the dry matter content used.

In a second embodiment of this fourth step of the method, the fractionation is performed using a chromatograpy technique carried out on a gel type resin.

The profiles obtained allow the separation of the fractions containing the highly branched glucose polymers with an optimum yield of between 40 and 45%.

Regardless of the method used, the profiles obtained allow the separation of the high molecular weight polysaccharide fraction corresponding to the soluble branched glucose polymers in accordance with the invention, from the low molecular weight oligosaccharide fractions essentially consisting of glucose and maltose and/or isomaltose.

The last step of the method in accordance with the invention therefore consists in collecting on the one hand the high molecular weight fractions corresponding to the highly branched glucose polymers, and on the other hand the low molecular weight fractions enriched with glucose and isomaltose and/or with maltose.

The high molecular weight products may be combined as they are, or precipitated with 3 volumes of ethanol, purified and dried under vacuum for 24 hours, or alternatively spray-dried, by any technique known to a person skilled in the art.

As for the compositions enriched with maltose and/or isomaltose, characterized in that they comprise the low molecular weight fractions of step d of the method in accordance with the invention, they may be used as they are, or hydrogenated by any hydrogenation technique moreover known to a person skilled in the art.

The particular physicochemical characteristics of the polymers according to the invention allow their applications in industry in particular the Paper-Carton, Textiles, Cosmetics, and particularly Pharmaceutical and Food industries, and still more particularly in the fields of enteral and parenteral nutrition, peritoneal dialysis as an osmotic agent, as a glycemia inhibiting agent, as an energy source during physical activities and as a digestion regulating agent.

As regards the particular field of peritoneal dialysis, the applicant has found, using a test of resistance to alpha-amylase, that a family of polymers in accordance with the invention was particularly suited to the preparation of solutions for peritoneal dialysis, as will be exemplified later. These polymers are used therein as an osmotic agent.

The invention thus relates to a composition for peritoneal dialysis, characterized in that it comprises, as osmotic agent, at least one soluble highly branched polymer having a reducing sugar content of less than 1%, and having:

a content of α-1,6 glucoside bonds greater than 8%, preferably of between 10 and 30%, a Mw, determined by light scattering, having a value of between $0.3 \times 10^5$ and $2 \times 10^5$ daltons, an osmolality, determined according to a test A, having a value of between 1 and 15 mOsm/kg.

According to a preferred variant of the invention, said polymer has:

a Mw, determined by light scattering, having a value of between $0.3 \times 10^5$ and $0.7 \times 10^5$ daltons, an osmolality, determined according to a test A, at least equal to 5 and less than 15 mOsm/kg.

The composition for peritoneal dialysis according to the invention may additionally comprise physiologically acceptable electrolytes, such as sodium, potassium, calcium, magnesium, chlorine, so as to avoid loss through transfer of electrolytes from the serum to the peritoneum.

This composition may be provided in solid form for preparation immediately before use or in liquid form, for example as an aqueous solution. In the latter case, the solution obtained by dissolving the highly branched polymers according to the invention in water should be clear and colorless. This solution should be preferably free of endotoxins, of peptidoglucans and of beta-glucans, and of nitrogenous contaminants resulting from the raw material, or from the enzymatic preparations used for its manufacture.

To this effect, the highly branched polymers used in said solution would have preferably been subjected to purification so as to remove any color or any undesirable contaminant such as proteins, bacteria, bacterial toxins, fibers, traces of metals, and the like.

This purification step may be carried out according to techniques known to the person skilled in the art.

The dialysis solution according to the invention may also comprise buffer solutions (lactate, acetate, gluconates in particular) and other additives such as amino acids, insulin, polyols such as for example sorbitol, erythritol, mannitol, maltitol and xylitol.

The addition of polyols to the composition, and preferably of polyols which are a pyrogenic and free of the impurities described above (endotoxins and other residues of bacterial origin in particular) makes it possible to increase the osmolarity of the solution more advantageously than glucose or maltose, because of their lower calorific value, their higher osmotic power and because they are not reducing.

The dialysis composition according to the invention is advantageous compared with the prior art products since the osmotic agent which it contains makes it possible to exert a lasting osmotic pressure and induces a low kinetics of appearance of glucose, while being stable to retrogradation, thus satisfying the principal criteria defined above.

Other characteristics and advantages of the invention will emerge on reading the nonlimiting examples described below.

EXAMPLE 1

A solution of starch derivatives having a dry matter content of 25% by weight is prepared by heating to 80° C., with slow and continuous stirring.

Two maltodextrins marketed by the Applicant Company under the names GLUCIDEX® 2 (substrate A) and GLUCIDEX® 6 (substrate B) at 250 g/l are used in this case.

This solution is cooled to 30° C., and the pH is brought to 6.8 with 1 N NaOH.

These solutions are then treated with purified glycogen branching enzyme extracted from the microorganism *B. stearothermophilus*.

The branching enzyme is added in an amount of 1600 U/g of substrate, and the temperature is gradually brought to 65° C.

The incubation is carried out with moderate stirring for 4 hours. The reaction is then stopped by reducing the pH to a value of 5 and by boiling for 6 minutes.

Table I below assembles, for both substrates tested, the results obtained in terms of contents of α-1,6 glucoside bonds, Mw values, reducing sugar contents and osmolality for the products obtained (product C from the substrate A and product D from the substrate B).

TABLE 1

|   | % of α-1,6 bonds | Mw $10^5$ daltons | % of reducing sugars | Osmolality mOsm/kg |
|---|---|---|---|---|
| A | 5.9 | 4.88 | 2 | 16 |
| B | 8.7 | 1.19 | 1.5 | 12 |
| C | 5.4 | 0.9 | 3.8 | 25 |
| D | 8 | 0.61 | 4.3 | 25 |

The content of α-1,6 glucoside bonds is substantially increased, but is not yet up to the desired values.

The Applicant Company found that an additional treatment should be carried out, by the action of enzymes which specifically hydrolyze the α-1,4 glucoside bonds (such as α-amylase, β-amylase or amyloglucosidase), or by the use of enzymes which complete the branching into α-1,6 bonds (such as α-transglucosidase), this being in the following manner.

For the additional enzymatic treatments, the solutions of the branched maltodextrins C and D are first of all brought to the temperature and the pH for the chosen enzyme.

1) For the additional treatment with α-amylase (LYSASE 2000 to 2444 BRU/g of enzymatic extract), said solutions of C or D are brought to a temperature of 60° C. and to a pH of 6.5 to 6.7, and 6 U of α-amylase are added per g of substrate.

The incubation is carried out for 30 minutes, and the reaction is stopped by boiling for 6 minutes.

2) For the additional treatment with β-amylase (BBA SPEZYME from GENENCOR), said solutions of C or D are brought to the temperature of 40° C. and to the pH of 4.9 to 5, and 30 U of β-amylase are added per g of substrate.

The incubation is carried out for 2 hours, and the reaction is stopped by boiling for 6 minutes.

3) For the additional treatment with amyloglucosidase (*A. niger* AMG from SIGMA AA-7420, at 40 U/mg of proteins), said solutions of C or D are brought to the temperature of 55° C. and to the pH of 4.7 to 4.9, and 20 U of AMG are added per g of substrate.

The incubation is carried out with moderate stirring for 2 hours, and the reaction is stopped by boiling for 6 minutes.

4) For the additional treatment with α-transglucosidase (L-AMANO α-TGase, activity of 27.7 μmol of glucose), said solutions of C or D are brought to the temperature of 55° C. and to the pH of 5 to 5.2, and 2 U of α-TGase are added per g of substrate.

The incubation is carried out for 1 hour, and the reaction is stopped by boiling for 6 minutes.

The physicochemical characteristics:

of the products E and F (obtained by additional treatment with α-amylase of the products C and D respectively), of the products G and H (obtained by additional treatment with β-amylase of the products C and D respectively), of the products I and J (obtained by additional treatment with AMG of the products C and D respectively) and of the products K and L (obtained by additional treatment with α-TGase of the products C and D respectively)

are then determined.

TABLE II

|   | % of α-1,6 bonds | Mw $10^5$ daltons | % of reducing sugars | Osmolality mOsm/kg |
|---|---|---|---|---|
| E | 8.3 | 0.72 | 3.8 | 29 |
| G | 8.4 | 0.76 | 22.5 | 132 |
| I | 9 | 0.49 | 55 | 320 |
| K | 9.6 | 1.2 | 22 | 153 |
| F | 7.4 | 0.44 | 8.7 | 52 |
| H | 7.2 | 0.51 | 23.8 | 141 |
| J | 7.8 | 0.47 | 50.5 | 301 |
| L | 12 | 0.69 | 28 | 192 |

The osmolality and the reducing sugar content which increase, indicate here the concomitant production mainly of glucose, of DP2 (maltose and isomaltose), which therefore has to be removed in order to obtain the highly branched glucose polymers in accordance with the invention.

It is chosen to use a fractionation by ultrafiltration on membrane with a cut-off of 5000 daltons (AMICON 5K membrane).

The results obtained for the products of ultrafiltration M, O, Q, S of the compounds E, G, I and K, respectively, on the one hand (which are therefore derived from GLUCIDEX® 2), and the products of ultrafiltration N, P, R, T of the compounds F, H, J and L, respectively, (which are therefore derived from GLUCIDEX® 6), are presented in the following Table III.

TABLE III

|   | % of α-1,6 bonds | Mw $10^5$ daltons | % of reducing sugars | Osmolality mOsm/kg |
|---|---|---|---|---|
| M | 10.2 | 0.89 | 0.42 | 1 |
| O | 15 | 0.75 | 0.3 | 1 |
| Q | 18.8 | 0.57 | 0.37 | 2 |
| S | 12.1 | 1.22 | 0.33 | 1 |
| N | 10.9 | 0.69 | 0.54 | 2 |
| P | 14.4 | 0.51 | 0.8 | 3 |
| R | 18.1 | 0.55 | 0.5 | 5 |
| T | 12.2 | 0.72 | 0.6 | 3 |

These results indicate the fact that the highly branched glucose polymers thus obtained exhibit the perfect equilibrium between the remarkably high (up to 18%) level of α-1,6 glucoside bonds, for products which have such a Mw value value and such a low osmolality value.

These highly branched glucose polymers can be easily mixed with other electrolytes to provide osmotic agents which are extremely efficient in peritoneal dialysis, or can be used as they are in compositions intended for regulating digestion, for parenteral and enteral nutrition, for compositions intended for diabetics, or in liquid drinks in order to reconstitute the energy reserves for athletes during a long physical effort.

It should be noted that in addition to these highly branched glucose polymers, the method also makes it possible to group together the fractions rich in maltose and/or isomaltose.

For example, in the case of the preparation of the products S and T (obtained from the combined treatment with the branching enzyme and with α-TGase), isomaltose and glucose are the sole coproducts manufactured (at the respective concentrations of 25 to 30 g/l and 75 to 80 g/l.

Likewise, in the case of the preparation of the products O and P (obtained from the combined treatment with the branching enzyme and β-amylase), maltose is the only coproduct manufactured (at the concentration of 130 g/l).

These low molecular weight fractions may therefore constitute advantageous sources of compositions rich in maltose and/or isomaltose.

EXAMPLE 2

The highly branched glucose polymers in accordance with the invention may also be prepared from standard corn starch. For this, 110 g on a dry basis of starch are suspended in one liter of water at room temperature and with slow and continuous stirring.

The pH is brought from 6.8 to 7 and the medium is left under these conditions for 15 minutes, adjusting the pH if necessary. The glycogen branching enzyme purified from *B. stearothermophilus* is added in an amount of 4000 U/g of substrate, the temperature being gradually brought to 72 to 75° C.

The incubation is then carried out with moderate stirring for 30 minutes, followed by cooling to a temperature of 65 to 68° C. The enzymatic reaction is carried out for 4 hours. The reaction is then stopped by reducing the pH to a value of 4.5 to 5, the medium is heated at boiling temperature for 6 minutes.

As in Example 1, the reaction is supplemented by treatments with β-amylase or with amyloglucosidase, and then by a step of ultrafiltration on a membrane with a cut-off of 5000 daltons under the conditions given in Example 1.

Table IV groups together the results obtained.

The standard corn starch is designated by the reference U; the product of treatment with the branching enzyme V, those additionally treated with β-amylase: W, with AMG: X; the ultrafiltered final products: Y and Z.

TABLE IV

|   | % of α-1,6 bonds | Mw $10^5$ daltons | % of reducing sugars | Osmolality mOsm/kg |
|---|---|---|---|---|
| U | 3.6 | 110 | <0.01 | Nd |
| V | 8.8 | 1.75 | 0.2 | 2 |
| W | 8.9 | 1.31 | 20.5 | 117 |
| Y | 16.3 | 1.38 | 0.1 | 2 |
| X | 7.9 | 0.55 | 55 | 357 |
| Z | 24.2 | 0.45 | 0.4 | 2 |

The products Y and Z obtained exhibit the same balanced profiles as those described in Example 1, and can therefore be advantageously used in the same fields of application.

EXAMPLE 3

Two other highly branched glucose polymers are prepared from two varieties of starch rich in amylopectin, under industrial conditions. They are two samples of acidic fluidified waxy corn starch with a level of fluidification WF of about 90, also marketed by the Applicant Company under the trade name CLEARGUM® CB 90.

Table V presents the operating conditions used to obtain the highly branched glucose polymers in accordance with the invention.

TABLE V

| Base | CLEARGUM CB90 | CLEARGUM CB90 |
|---|---|---|
| Solubilization | Continuous laboratory cooker containing 25% DM | Continuous laboratory cooker containing 25% DM |
| 1st enzyme | Branching enzyme 50 000 U/ml - 1 ml/100 g dry basis | Branching enzyme 50 000 U/ml - 1 ml/100 g dry basis |

TABLE V-continued

| Base | CLEARGUM CB90 | CLEARGUM CB90 |
|---|---|---|
| 1st enzymatic treatment | 70° C. pH 6.8 22 h and then deactivation 1 h at 90–95° C. | 70° C. pH 6.8 22 h and then deactivation 1 h at 90–95° C. |
| 2nd enzyme | Amyloglucosidase OPTIDEX L300A 0.08 ml/100 g dry basis + 0.08 ml/100 g dry basis after 1 h 30 min | β-amylase SPEZYME BBA 0.2 ml/100 g dry basis |
| 2nd enzymatic treatment | 55° C. pH 4.7 - 2 h and 3 h and then deactivation 1 h at 90–95° C. | 40° C. pH 5 2 h and then deactivation 1 h at 90–95° C. |
| Purification | Filtration on 8 and then 0.22 µm - membrane ultrafiltration PCI Membrane Systems ES209 (9000 Da) - Charcoal treatment NORIT SX+ 5% dry basis pH 5 70° C. 1 h - adjustment of pH to 5.8 and filtration on 8 and then 0.22 µm | Adjustment of pH to 3.5 over 18 h - Centrifugation 5000 rpm 10 min - Filtration on filtering earth and then 8 µm - Membrane ultrafiltration PCI Membrane Systems ES209 (9000 Da) - Charcoal treatment NORIT SX+ 5% dry basis pH 5 70° C. 1 h - Filtration on 8 and then 0.22 µm |
| Recovery | Concentration to dryness in a rotary evaporator under vacuum | Concentration to dryness in a rotary evaporator under vacuum |

Table VI presents the results obtained in terms of content of α-1,6 glucoside bonds, of Mw values, of reducing sugar contents and of osmolality for the products obtained:

"a" relates to the product obtained from CLEARGUM® CB 90 after treatment with the branching enzyme and amyloglucosidase and "b" relates to the product obtained from CLEARGUM® CB 90, after treatment with the branching enzyme and β-amylase.

TABLE VI

| | % of α-1,6 bonds | Mp $10^5$ daltons | % of reducing sugars | Osmolality mOsm/kg |
|---|---|---|---|---|
| "a" | 19.4 | 0.33 | 1 | 12 |
| "b" | 14.3 | 0.68 | 0.7 | 6 |

These results indeed show that the method used makes it possible to obtain highly branched glucose polymers in accordance with the invention regardless of the starch or starch derivative base chosen.

EXAMPLE 4

Aqueous solutions of highly branched polymers in accordance with the invention are prepared, and they are brought into contact with an amylase of pancreatic origin. The amylase hydrolysis is monitored over time by measuring the reducing sugars formed and by measuring the glucose which appears in the reaction medium. This test makes it possible to evaluate the resistance of the polymers to amylase hydrolysis, which is an essential criterion in the choice of an osmotic agent for a dialysis solution.

Several polymers in accordance with the invention are tested in comparison with icodextrin (prior art osmotic agent). The polymers are chosen so as to have a molecular weight close to the latter:

Products A and B as prepared in accordance with Example 3 and product Z as prepared in accordance with Example 2.

The icodextrin is manufactured in accordance with patent EP 667,356 cited in the description.

A maltose control is prepared in order to validate the in vitro model of enzymatic digestion.

The operating conditions for the amylase digestion are the following:

accurately weigh about 0.6 g of product to be tested, add 150 ml of Na maleate buffer pH 7 at 0.1 mol/l, stir until the product dissolves, remove 1.5 ml of the solution obtained (initial solution=si), place the bottles on a water bath for 15 minutes, so that the temperature of the solution is 37° C., add 0.15 g of pig pancreatin (α-amylase of animal origin), incubate at 37° C. on a thermostated bath, with stirring, for 300 minutes RT, collect samples of 1.5 ml at the times: 15, 30, 45, 60, 90, 120, 180, 240, 300 minutes, stop the enzymatic reaction by placing the samples in a bath to dryness at 100° C. for 10 minutes, assay the glucose on the samples, in order to simulate the impact of the studied product on glycemia, assay the reducing sugars on the samples in order to study the rate of hydrolysis.

For the glucose assay, a colormetric method is used which is carried out on a HITACHI 704 automatic machine (ROCHE). The reagent used is a reagent containing the enzymes GOD/PAP (glucose oxidase/peroxidase). The volume of reagent used is 500 microliters, the sample volume is 5 microliters and the reaction temperature is 30° C.

The method used for the assaying of reducing sugars is the SOMOGYI NELSON method. 200 microliters of sample are introduced into a stoppered tube, and 200 microliters of working solution (sodium tartrate and copper sulfate reagents) are added. The medium is heated to boiling temperature, and the arsenomolybdic reagent is added after cooling, followed by water. The solution obtained is deposited in a microplate, and then the absorbence is read using a microplate reader at a wavelength of 520 nanometers.

The results are presented in the following tables:

1. Kinetics of appearance of glucose (as % released on a dry basis)

| Time (in min) | MALTOSE | A | B | Z | ICODEXTRIN |
|---|---|---|---|---|---|
| si | 0.26 | 3.35 | 0.00 | 0.53 | 0.28 |
| 0 | 0.26 | 4.75 | 0.93 | 1.19 | 1.96 |
| 15 | 0.79 | 5.31 | 1.59 | — | 3.07 |
| 30 | 1.06 | 5.68 | 1.96 | 2.11 | 3.63 |
| 45 | 1.59 | 5.86 | 2.24 | — | 3.91 |
| 60 | 2.12 | 6.14 | 2.52 | 2.37 | 4.19 |
| 90 | 2.65 | 6.52 | 2.89 | — | 4.75 |
| 120 | 3.44 | 6.61 | 3.17 | 2.90 | 5.31 |
| 180 | 5.03 | 7.26 | 4.76 | 3.43 | 6.15 |
| 240 | 6.35 | 8.10 | — | 3.96 | 6.99 |
| 300 | 7.68 | 8.38 | 5.41 | 4.22 | 7.82 |

2. Kinetics of appearance of the reducing sugars (as % on a dry basis)

| Time (in min) | MALTOSE | A | B | Z | ICODEXTRIN |
|---|---|---|---|---|---|
| si | 51.01 | 5.76 | 0.88 | 1.45 | 2.74 |
| 0 | 49.82 | 18.34 | 18.04 | 8.92 | 31.07 |
| 15 | 47.94 | 19.33 | 18.96 | — | 30.39 |
| 30 | 48.29 | 20.00 | 19.04 | 11.00 | 32.53 |
| 45 | 48.55 | 20.25 | 19.78 | — | 32.46 |
| 60 | 48.84 | 19.92 | 20.80 | 11.10 | 32.95 |
| 90 | 49.42 | 20.37 | 19.42 | — | 34.16 |
| 120 | 47.15 | 21.68 | 21.04 | 12.16 | 34.40 |
| 180 | 48.87 | 22.46 | 21.79 | 12.22 | 36.64 |
| 240 | 50.90 | 23.05 | 23.11 | 12.29 | 37.03 |
| 300 | 52.20 | 22.67 | 22.88 | 13.64 | 37.06 |

3. Summary analysis of the results

| PRODUCTS TESTED | % of glucose released at 300 min | % of reducing sugars formed at 300 min | Content of α-1,6 bonds in % | Molar mass (daltons) |
|---|---|---|---|---|
| MALTOSE | 7.41 | 52.20 | 0 | 342 |
| A | 5.03 | 16.91 | 19.4 | 33 000 |
| B | 5.41 | 22.88 | 14.3 | 68 000 |
| Z | 3.69 | 12.19 | 24.2 | 45 000 |
| ICODEXTRIN | 7.54 | 34.32 | 6.5–8 | 12 000–20 000 |

It is observed from the results obtained that the higher the level of branching (the level of α-1,6 bonds), the lower the amylase hydrolysis.

The latter is generally dependent on the molecular weight. Thus, the higher the level of branching and the lower the molecular weight, the less the molecule is attacked by amylase.

For a use in intraperitoneal dialysis, the products A and Z are particularly suitable and have a resistance which is markedly higher than icodextrin, which means that these products have a definite advantage in terms of duration of osmotic power and of glycemic power, for a similar molecular weight.

EXAMPLE 5

Aqueous solutions of highly branched polymers in accordance with the invention are prepared, and they are brought into contact with an amylase of pancreatic origin and with an intestinal amyloglucosidase (acetonic intestine powder). The hydrolysis is monitored over time by measuring the glucose which appears in the reaction medium. This test makes it possible to evaluate the resistance of the polymers to hydrolysis by the enzymes involved in the digestion of food carbohydrates, which is an essential criterion in the choice of a food ingredient entering into the composition of formulations for use by athletes or intended for enteral and parenteral nutrition.

Several polymers in accordance with the invention are tested in comparison with icodextrin, glycogen, and a standard maltodextrin. The polymers chosen are the following:

Products A are prepared in accordance with Example 3, products Y are prepared in accordance with Example 2, and products Y' prepared according to Example 2 from an amylopectin-rich starch treated with the branching enzyme and ultrafiltered.

The icodextrin is manufactured in accordance with patent EP 667.356 cited in the description. The glycogen is a bovine liver glycogen provided by the company SIGMA-ALDRICH.

A standard maltodextrin control is prepared in order to validate the in vitro model of enzymatic digestion.

The operating conditions for the enzymatic digestion are the following:

Accurately weigh about 0.6 g of product to be tested.
Add 150 ml of Na maleate buffer pH 7 at 0.1 mol/l.
Stir until the product dissolves.
Remove 1.5 ml of the solution obtained.
Place the bottles on a water bath for 15 minutes, so that the temperature of the solution is 37° C.
Add 0.15 g of pig pancreatin.
Incubate at 37° C. on a thermostated bath, with stirring, for 30 minutes RT.
Collect samples of 1.5 ml at the times: 0 min at 30 minutes.
Stop the enzymatic reaction by placing the samples in a bath to dryness at 100° C. for 10 minutes.
Add 0.15 g of rat intestinal mucous membrane.
Incubate for 5 h 30 min at 37° C. on a thermostated water bath, with stirring.
Collect 1.5 ml samples every 60 minutes at the times 60; 120; 180; 240; 300; 330 and 360 minutes.
Stop the enzymatic reaction by placing the samples in a bath to dryness at 100° C. for 10 minutes.
Assay the glucose on the samples in order to calculate the percentage hydrolysis of the product studied.
For the glucose assay, the same method as in Example 4 is used.

The results are presented in the tables below:

1. Kinetics of appearance of glucose (in % released on a dry basis)

| | Time (in min) | Standard MALTOD. | GLYCOGEN | A | Y | Y' | ICODEXTRIN |
|---|---|---|---|---|---|---|---|
| Pancreatic amylase | 0 | 0 | 0 | 0 | 0 | 0 | 0 |
| | 15 | 0.79 | 2.87 | 2.61 | 2.17 | 3.90 | 3.35 |
| | 30 | 1.06 | 3.30 | 2.70 | 2.71 | 4.74 | 3.63 |
| Intestinal amylase | 60 | 20.88 | 12.62 | 9.77 | 13.71 | 16.31 | 15.09 |
| | 90 | 38.59 | 22.81 | 16.66 | 23.34 | 28.29 | 26.96 |
| | 120 | 52.07 | 31.41 | 23.17 | 32.17 | 40.28 | 37.86 |
| | 150 | 62.90 | 39.45 | 28.66 | 39.22 | 48.64 | 47.22 |
| | 180 | 70.83 | 46.04 | 32.75 | 44.52 | 57.84 | 55.88 |

-continued

1. Kinetics of appearance of glucose (in % released on a dry basis)

| Time (in min) | Standard MALTOD. | GLYCOGEN | A | Y | Y' | ICODEXTRIN |
|---|---|---|---|---|---|---|
| 210 | 78.76 | 51.50 | 37.03 | 49.00 | 64.53 | 63.01 |
| 240 | 83.78 | 56.09 | 39.64 | 52.39 | 68.71 | 69.01 |
| 270 | 88.81 | 59.96 | 42.62 | 54.56 | 72.33 | 72.09 |
| 300 | 91.18 | 62.40 | 45.50 | 57.27 | 75.96 | 76.28 |
| 330 | 93.03 | 64.26 | 47.27 | 58.63 | 79.44 | 78.37 |
| 360 | 94.36 | 65.84 | 51.64 | 60.80 | 81.11 | 80.89 |

2. Summary analysis of the results

| PRODUCTS TESTED | % of glucose released at 360 min | Level of α-1,6 bonds in % | Molar mass (daltons) |
|---|---|---|---|
| STANDARD MALTODEXTRIN | 94.36 | 0 | 3000–5000 |
| GLYCOGEN | 65.84 | 10 | $10^6$–$10^7$ |
| A | 51.64 | 19.4 | 33 000 |
| Y | 60.80 | 16.3 | 138 000 |
| Y' | 81.11 | 7.9 | 133 000 |
| ICODEXTRIN | 80.89 | 6.5–8 | 12 000–20 000 |

The maltodextrins according to the invention are particularly suitable for use in nutrition for athletes or more generally for regulating glycemia. The products A and Y according to the invention make it possible to obtain a percentage of release of glucose of between 50 and 70%, that is a resistance to hydrolysis which is markedly higher than conventional maltodextrins and comparable to glycogen, which means that these products have a definite advantage in terms of glycemic power and can thus advantageously constitute a glycogen substitute since they exhibit similar digestion characteristics.

The invention claimed is:

1. A food composition, comprising soluble highly branched glucose polymers, said highly branched glucose polymers having a reducing sugar content of less than 1%, and wherein said glucose polymers have:
   a content of α-1,6 glucoside bonds greater than 10%,
   a Mw value, determined by light scattering, of between $0.3 \times 10^5$ and $2 \times 10^5$ daltons,
   an osmolality value, determined according to a test A, of between 1 and 15 mOsm/kg.

2. The food composition according to claim 1, wherein said glucose polymers have:
   a Mw value, determined by light scattering, of between $0.5 \times 10^5$ and $1.5 \times 10^5$ daltons,
   an osmolality, determined according to a test A, at least equal to 1 and less than 2 mOsm/kg.

3. The food composition according to claim 1, wherein said glucose polymers have:
   a Mw value, determined by light scattering, of between $0.5 \times 10^5$ and $0.8 \times 10^5$ daltons,
   an osmolality, determined according to a test A, at least equal to 2 and less that 5 mOsm/kg.

4. The food composition according to claim 1, wherein said glucose polymers have between 12 and 30% of α-1,6 glucoside bonds.

5. The food composition according to claim 1, wherein said glucose polymers have between 15 and 30% of α-1,6 glucoside bonds.

6. The food composition according to claim 1, wherein said glucose polymers have:
   a Mw value, determined by light scattering, of between $0.3 \times 10^5$ and $0.7 \times 10^5$ daltons,
   an osmolality, determined according to a test A, at least equal to 5 and less than 15 mOsm/kg.

7. The food composition according to claim 1, wherein said composition is a liquid.

8. The food composition according to claim 1, wherein said composition is a solid.

9. A method for preparing the food composition according to claim 1, comprising the following steps:
   preparing an aqueous starch suspension or a solution of starch derivative having a dry matter content at least equal to 1% by weight,
   treating said suspension or said solution with at least one branching enzyme at a temperature comprised between 25 and 80° C. for a period of 1 to 24 hours,
   adding at least one enzyme selected from the group consisting of α-amylase, β-amylase, amyloglucosidase and α-transgluscosidase to act on the suspension or on the solution thus obtained,
   fractionating by at least one technique selected from the group consisting of membrane separations and chromatographies,
   recovering high molecular weight fractions and low molecular fractions,
   collecting highly branched glucose polymers corresponding to the high molecular weight fractions obtained, and
   adding said highly branched glucose polymers to said food product.

10. The method according to claim 9, wherein the branching enzyme is selected from the group consisting of glycogen branching enzymes, starch branching enzymes and any mixtures of theses enzymes.

11. The method according to claim 9, wherein the fractionation technique is selected from the group consisting of the technique of separation on an ultrafiltration membrane and the technique of chromatographic separation on a gel type support.

12. The method according to claim 9, wherein the fractionation technique is the technique of chromatographic separation on a gel type support.

13. An enteral and parenteral nutrition composition, comprising the composition according to claim 1.

14. A peritoneal dialysis solution, comprising at least one soluble highly branched polymer according to claim 1.

15. The dialysis solution according to claim 14, wherein said soluble highly branched polymer has:

a Mw value, determined by light scattering, of between $0.3 \times 10^5$ and $0.7 \times 10^5$ daltons, an osmolality, determined according to a test A, at least equal to 5 and less that 15 mOsm/kg.

16. The solution according to claim 14, comprising a polyol selected from the group consisting of sorbitol, mannitol, maltitol, xylitol and erythritol.

17. The solution according to claim 14, further comprising buffer solutions.

18. The solution according to claim 17, wherein said buffer solution comprises lactate acetate.

19. The solution according to claim 17, wherein said buffer solution comprises gluconate salts.

* * * * *